United States Patent
Chatterjee et al.

(10) Patent No.: US 8,093,391 B2
(45) Date of Patent: Jan. 10, 2012

(54) PROCESS FOR THE PREPARATION OF SUBSTANTIALLY PURE PALONOSETRON AND ITS ACID SALTS

(75) Inventors: Sugata Chatterjee, Vadodara (IN); Ajay Singh Rawat, Vadodara (IN); Anil V. Pawar, Latur (IN); Jetti Rajanikanth, Vizag (IN); Penigandla Venkateswarlu, Prakasam (IN)

(73) Assignee: Sterling Biotech Research Center, Gujarat (IN)

( * ) Notice: Subject to any disclaimer, the term of this patent is extended or adjusted under 35 U.S.C. 154(b) by 40 days.

(21) Appl. No.: 12/652,090

(22) Filed: Jan. 5, 2010

(65) Prior Publication Data

US 2011/0021778 A1    Jan. 27, 2011

(30) Foreign Application Priority Data

Jul. 21, 2009    (IN) .......................... 1677/MUM/2009

(51) Int. Cl.
| | |
|---|---|
| *C07D 401/00* | (2006.01) |
| *C07D 211/06* | (2006.01) |
| *C07D 211/40* | (2006.01) |
| *C07D 211/54* | (2006.01) |
| *C07D 211/00* | (2006.01) |
| *A61K 31/44* | (2006.01) |
| *A61K 31/445* | (2006.01) |
| *A01N 43/40* | (2006.01) |

(52) U.S. Cl. .......... 546/99; 546/200; 546/204; 546/208; 546/216; 546/243; 514/296; 514/325; 514/327; 514/330

(58) Field of Classification Search .................. 514/296; 546/97

See application file for complete search history.

(56) References Cited

U.S. PATENT DOCUMENTS

2008/0058367 A1 *    3/2008    Palle et al. .................... 514/296

OTHER PUBLICATIONS

Harwood et al., Experimental Organic Chemistry: Standard and Microscale, Wiley-Blackwell, 1999, p. 131-142.*

Huibers and Katrizky, Correlation of the Aqueous Solubility of Hydrocarbons and Halogenated Hydrocarbons with Molecular Structure, J. Chem. Inf. Comput. Sci., 38(2), 1998.*

Lambert et al.,Halogenation of Aromatic Compounds by N-Bromo- and N-Chlorosuccinimide under Ionic Conditions J. Org. Chem., 30(1) 1965 p. 305.*

* cited by examiner

*Primary Examiner* — Rita Desai
*Assistant Examiner* — Ben S Michelson
(74) *Attorney, Agent, or Firm* — Barnes & Thornburg LLP; Mark J. Nahnsen

(57) ABSTRACT

This invention relates to an improved and scalable process for the preparation of substantially pure palonosetron and its acid addition salts, in particular hydrochloride (I) which comprises of, (a) converting intermediate (IIa) as such or as its freebase (II) to a crude mixture of diastereomeric palonosetrons (VIII) or (VIIIa) contaminated with varying amounts of unconverted intermediate (II) or (IIa) via hydrogenation under pressure with an appropriately chosen hydrogenation catalyst in an suitable organic solvent.

(b) making the resulting crude mixture of diastereomeric palonosetrons (VIII) or (VIIIa) contaminated with varying amounts of unconverted intermediate (II) or (IIa) substantially free from (II) or (IIa) via halogenation reaction.

(c) Finally, converting the resulting diastereomeric palonosetron (VIII) or its hydrochloride (VIIIa) substantially free from intermediate (II) or (IIa) to the desired palonosetron hydrochloride (I) in substantially pure form via selective crystallization from a suitable single or mixture of organic solvents.

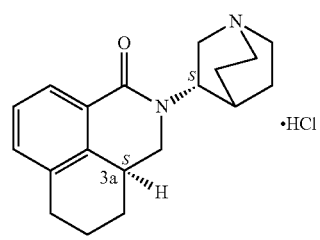

9 Claims, No Drawings

PROCESS FOR THE PREPARATION OF SUBSTANTIALLY PURE PALONOSETRON AND ITS ACID SALTS

This application claims priority to Indian Patent Application No. 1677/Mum/2009 Filed Jul. 21, 2009 which is herein incorporated by reference.

The present invention relates to an improved process for the preparation of substantially pure Palonosetron and its acid addition salts.

Palonosetron is described chemically as (3aS)-2-[(S)-1-azabicyclo[2.2.2]oct-3-yl]-2,3,3aS,4,5,6-hexahydro-1H-benz[de]isoquinolin-1-one. It is available and administered as its hydrochloride salt (Aloxi). It is a 5-hydroxytryptamine (serotonin) subtype 3 receptor antagonist having little or no affinity for other bioreceptors, including other serotonergic receptors $5\text{-HT}_1$, $5\text{-HT}_2$ and $5\text{-HT}_4$. It is used in the prevention of acute as well as delayed nausea and vomiting associated with initial and repeat course of moderately and highly emetogenic cancer chemotherapy.

BACKGROUND

Palonosetron is described as (3aS)-2-[(S)-1-azabicyclo[2.2.2] oct-3-yl]-2,3,3aS, 4,5,6-hexahydro-1H-benz [de] isoquinolin-1-one having the structural formula I and is administered as its hydrochloride salt (Aloxi).

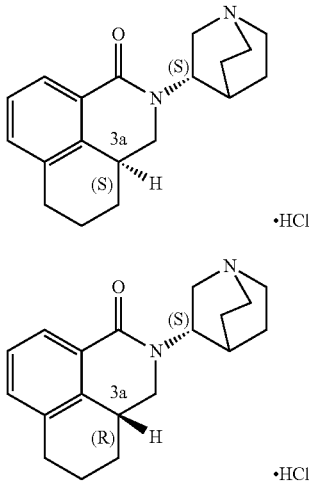

Palonosetron hydrochloride is a white to off-white crystalline powder and is freely soluble in water. It contains two chiral centers and is synthesized as a single diastereomer wherein both have S, S absolute configurations. The first synthesis of Palonosetron hydrochloride is described in EP 0,430,190 A2 and its equivalent U.S. Pat. No. 5,202,333 by Berger et. al. The authors discuss a process wherein palonosetron hydrochloride (I) is prepared from immediate precursor intermediate (II) by way of its reduction at high pressure to diastereomeric palonosetron hydrochloride followed by crystallization of the resulting diastereomeric mixture two to three times from ethanol.

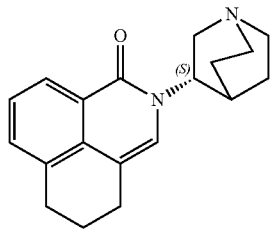

The problem features, albeit of essential significance of the disclosed process, are described below.

Firstly, the chemical purity of the diastereomeric palonosetrons obtained by the hydrogenation of intermediate II is not mentioned. Secondly the obtained diastereomeric mixture is purified to the desired (3aS, S) diastereomer by repeated crystallization from ethanol resulting in significant yield loss. Finally, the desired palonosetron hydrochloride (I) is contaminated with 1.0% or above of the undesired 3aR, S-diastereomer (Ia).

The authors also disclose a slightly revised process in *Journal of Medicinal Chemistry*, 1993, 36(18) wherein is described an additional example for the reduction of intermediate II with 10% Pd/C (62% wet w/w) in tetrahydrofuran under a hydrogen atmosphere for fifteen days. Here also there is no mention of the chemical purity of diastereomeric palonosetrons. Also the diastereomeric purity of the final product (I) is reported to be 99.00% only.

Another U.S. Pat. No. 5,510,486 by Robinson III et. al. provides a process for the preparation of palonosetron and its pharmaceutically acceptable salts, following the strategy in a general scheme 01.

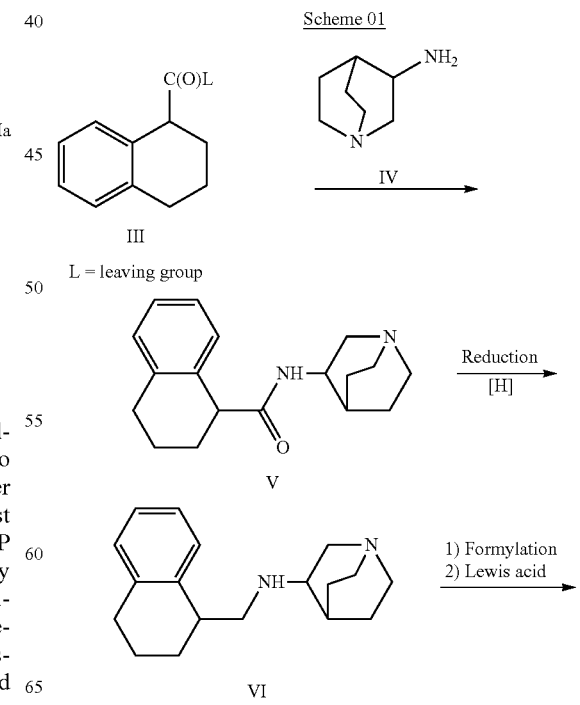

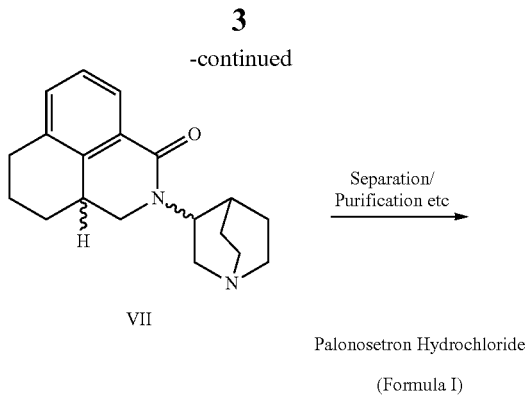

VII

Separation/ Purification etc →

Palonosetron Hydrochloride (Formula I)

This process providing palonosetron hydrochloride (I) by using different starting materials does not discloses the diastereomeric purity of the final product.

Another prior art U.S. Pat. No. 5,567,818 by Kowalczyk, also published in *Heterocyles*, 1996, 43(7) describes a process for the preparation of palonosetron hydrochloride (I) wherein intermediate (II) is converted to palonosetron hydrochloride (I) following a process essentially similar to those discussed in the earlier prior arts i.e EP 0,430,190 A2 etc. However the disclosed process affords palonosetron hydrochloride (I) showing only 99% diastereomeric purity.

Another publication *Organic Process & Development* 1997, 1, 117-180 by Bruce A. Kowalczyk & Norman H. Dyson, discusses hydrogenation of intermediate II to diastereomeric palonosetrons by various catalysts under different reaction conditions. Mentioned therein is the equilibration of undesired (3aR,S) diastereomer as its hydrochloride (Ia) to the desired palonosetron hydrochloride (I) via hydrogen activated palladium catalyst under a nitrogen atmosphere. The publication discloses the resulting product mixture of palonosetron hydrochloride (I) and the undesired (3aR,S) diastereomer (Ia) contaminated with ~1.00% of intermediate II as its hydrochloride in one of the examples of equilibration. The amount of intermediate II or its hydrochloride present before equilibration or after reduction with various catalysts and under varying conditions can be envisaged by the conversion listed in the Tables 1 & 2 of this publication which indicate presence of a maximum of ~82.0% and a minimum of 1.0% of the intermediate II or its hydrochloride although a sufficiently pure mixture of desired palonosetron hydrochloride (I) and its undesired 3aR,S diastereomer (Ia) has been employed for the equilibration reaction. However the publication does not mention anything on separation of the unwanted intermediate II from the diastereomeric palonosetrons. The palonosetron hydrochloride (I) produced in this publication has been reported to contain only 99.2% of the desired (S, S) isomer.

Another prior art US 2008/0058367 A1 describes a process for the purification of palonosetron or its salts. In this publication the crude reaction product after the reduction of intermediate II containing 52.61% palonosetron hydrochloride (I), 45.19% of its undesired 3aR,S-diastereomer (Ia) and 0.65% of intermediate II is purified by a cycle of operations described below which may appear remarkably cumbersome.

First step is slurry wash of the crude reaction product obtained after reduction with ethanol for 2.0 hours followed by filtration and suck drying for 3.0 hours to yield palonosetron hydrochloride (I) having 93.71% of the desired (3aS, S) isomer, 6.13% of the undesired (3aR, S) diastereomer (Ia) and 0.08% of the unreacted intermediate II.

Second step involves replacement of ethanol traces by suspending the above obtained palonosetron hydrochloride (I) in methanol and removing methanol completely by distillation at 55 to 60° C. Third step involves suspending again the so obtained palonosetron hydrochloride (I) in methanol, diluting it further with methanol, passing the obtained suspension through celite, concentrating the filtrate to a marked level, stirring the contents first between 25-35° C. then between 0-5° C. for 2.0 hours and then finally filtering the precipitated solid followed by vacuum drying. This leads to a palonosetron hydrochloride I having 99.72% of the desired (3aS,S) isomer, 0.18% of the undesired (3aR,S) diastereomer (Ia) and 0.04% of the intermediate II.

This publication also discloses a reprocessing method wherein the mixture of diastereomeric palonosetron contaminated with more than 1.0% of unconverted intermediate II obtained after reduction of intermediate II is resubjected to the hydrogenation reaction conditions and purified via the tedious purification process as discussed in the earlier texts to yield palonosetron hydrochloride (I) which is 99.75% pure by chiral HPLC.

Both the methods discussed in this publication have the following drawbacks. Firstly, the purification method used does not eliminate the unwanted intermediate II completely. The yield after performing the tedious purification process has not been disclosed. Nonetheless it may not be unreasonable to envisage a yield substantially below commercial acceptance.

The reprocessing method of resubjecting the crude mixture of palonosetron hydrochloride (I), its undesired (3aR, S) diastereomer (Ia) and intermediate of formula II wherein intermediate II as its hydrochloride is more than 1.00% to the hydrogenation conditions, as demonstrated by the authors, does not ensure lowering of the amount of intermediate II or its hydrochloride.

As seen in the discussed prior arts, various methods for the preparation of palonosetron and its pharmaceutically acceptable salts, and its purification from the undesired isomer and unreacted starting materials have been provided. However the issue of the complete removal of the unreacted intermediate II or its hydrochloride present in varying amounts in palonosetron or its hydrochloride (I) carried forward from the reduction step still remains in spite of efforts along this direction are reported in few prior arts, e.g., US 2008/0058367 A1 via tedious purification procedures without commensurate success.

Thus the need to develop an economically and operationally viable purification process to separate the unwanted intermediate II or its hydrochloride and the undesired 3aR, S diastereomer (Ia) efficiently from a crude mixture of palonosetron hydrochloride (I), undesired (3aR,S) diastereomer (Ia) and unreacted intermediate II to provide palonosetron hydrochloride (I) in substantially pure form is required.

SUMMARY

The aim of the present invention is to provide an improved and scalable procedure for the preparation of palonosetron and its acid addition salts substantially free from any contamination by unreacted precursor II as such or as its hydrochloride and also its undesired (3aR, S) diastereomer (Ia).

The objectives as mentioned above will be apparent in the following detailed description.

DETAILED DESCRIPTION

The process of the present invention is illustrated in scheme 02 as described below.

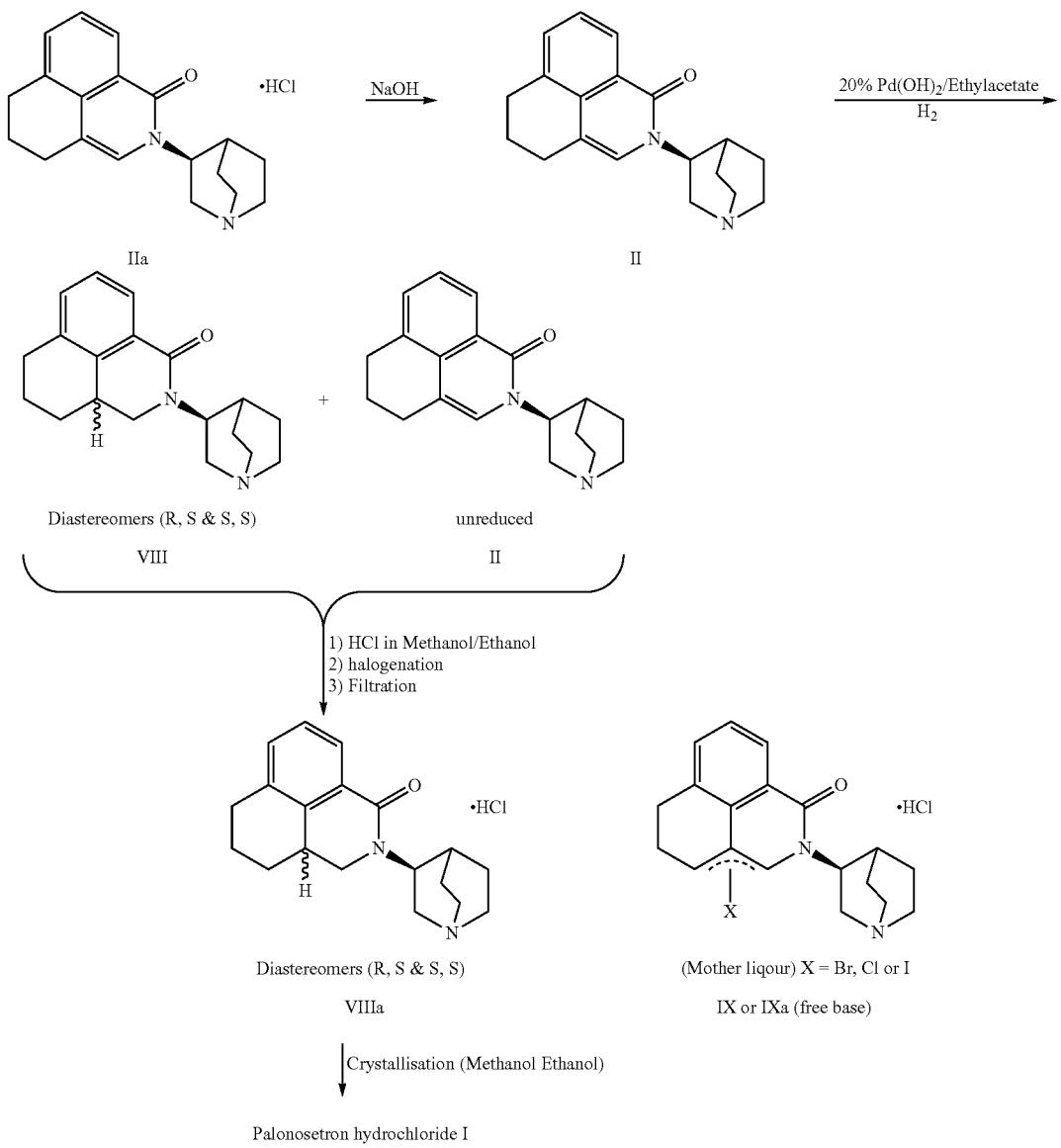

Scheme 02

The present disclosure relates to an improved and scalable procedure for the preparation of substantially pure palonosetron and its acid addition salts, which comprises of,
(1) Converting intermediate of formula II or IIa to the crude diastereomeric mixture of 3aR, S & 3aS, S palonosetrons VIII or VIIIa contaminated with varying amounts of unreduced intermediate II or IIa via hydrogenation reaction with an appropriately chosen hydrogenation catalyst in a suitable organic solvent.
(2) Treating the obtained crude diastereomeric palonosetrons (VIII) or hydrochloride (VIIIa) with a suitable chosen halogenating agent in the presence or absence of free radical initiator in a suitable single or a mixture of solvents to remove selectively the unreduced starting material II or IIa by virtue of its conversion to an easily removable intermediate of likely formula IX or IXa and yield diastereomeric palonosetron (VIII) or its hydrochloride (VIIIa) substantially free from intermediate II or IIa.
(3) Finally, crystallizing the obtained substantially pure diastereomeric mixture of palonosetron (VIII) or its hydrochloride (VIIIa) in a suitable single or a mixture of organic solvents to yield the desired palonosetron or its hydrochloride (I) in a substantially pure form.

The present invention further provides a process wherein the reduction of intermediate II or IIa to the diastereomeric palonosetrons (VIII) or (VIIIa) having varying amounts of unconverted intermediate II or IIa is carried out under standard hydrogenation conditions with an appropriate hydrogen catalyst under pressure varying from atmospheric to about 100 psi.

The present invention further provides a process wherein the hydrogenation reaction of intermediate II or IIa to the diastereomeric palonosetrons (VIII) or (VIIIa) having varying amounts of unconverted intermediate II or IIa is performed from temperatures ranging from ambient to reflux temperature of the chosen solvent.

The present invention further provides a process wherein the suitable catalyst used for the hydrogenation of intermediate II or IIa to the diastereomeric palonosetrons (VIII) or (VIIIa) having varying amounts of unconverted intermediate II or IIa is chosen from 20% palladium hydroxide on carbon, 10% palladium on carbon, Pearlmans catalyst (50% water 20% palladium content), palladium/barium sulphate, rhodium on alumina and rhodium on carbon.

The present invention further provides a process wherein the suitable catalyst used for the hydrogenation of intermediate II or IIa to the diastereomeric palonosetrons (VIII) or (VIIIa) having varying amounts of unconverted intermediate II or IIa is optionally recovered and reused without activation for affecting the same conversion.

The present invention further provides a process wherein the suitable solvent used for the hydrogenation of intermediate II or IIa to the diastereomeric palonosetrons (VIII) or (VIIIa) having varying amounts of unconverted intermediate II or IIa is chosen from ethanol, dimethylformamide, acetic acid, ethyl acetate, tetrahydrofuran, toluene and the likes thereof.

The present invention further provides a process wherein the crude diastereomeric palonosetron (VIII) or (VIIIa) contaminated with varying amounts of unreduced intermediate (II) or (IIa) is subjected to the halogenation reaction with a suitable halogenating reagent in the presence or absence of a suitable free radical initiator, in a suitable single or a mixture of suitable organic solvent which converts the unreduced intermediate (II) or (IIa) to the proposed easily separable halogenated intermediate (IX) or (IXa) to provide diastereomeric palonosetron (VIII) or its hydrochloride (VIIIa) substantially free from the unreduced intermediate (II) or (IIa).

The present invention further provides a process wherein the halogenation reaction may optionally be performed more than once on the crude palonosetron (VIII) or (VIIIa) to remove the varying amounts of II or IIa present in it.

The present invention further provides a process wherein the suitable halogenating reagent is chosen from bromine, chlorine, iodine, N-bromosuccinimide, N-chlorosuccinimide, N-iodosuccinimide, bromine-triphenylphosphine, N-bromopthalimi-de etc and the likes thereof.

The present invention further provides a process wherein 0.01 to 1.0 molar equivalent of the chosen halogenating reagent is used.

The present invention further provides a process wherein the suitable halogenating reagent is added neat or after dilution with the reaction solvent.

The present invention further provides a process wherein the suitable halogenating reagent is added at temperatures ranging from ambient to reflux temperature of the reaction solvent.

The present invention further provides a process wherein the suitable halogenating reagent is used preferably with or without a free radical initiator. When used the suitable free radical initiator is chosen from benzoyl peroxide, azobisisobutyronitrile, light etc and the likes thereof.

The present invention further provides a process wherein the halogenation reaction of the crude diastereomeric palonosetron (VIII) or (VIIIa) is performed in an alcoholic or a non-alcoholic solvent or a mixture of alcoholic solvents or a mixture of alcoholic and non-alcoholic solvent.

The alcoholic solvent may be chosen from a C-1 to C-8 linear or branched chain aliphatic alcohol, most preferably methanol and/or ethanol.

The non-alcoholic organic solvent may be chosen from tetrahydrofuran, dimethylformamide, diethylether, dimethoxyethane, dichloromethane, chloroform, carbontetrachloride etc.

The present invention further provides a process wherein the halogenation reaction to remove the varying amounts of unreduced intermediate (II) or (IIa) present in crude diastereomeric palonosetron (VIII) or (VIIIa) is performed from ambient to reflux temperature of the chosen suitable organic solvent.

The present invention further provides a process wherein the halogenation reaction to remove the varying amounts of unreduced intermediate (II) or (IIa) present in crude diastereomeric palonosetron (VIII) or (VIIIa) is performed under acidic, basic or neutral conditions.

The present invention further provides a process wherein the diastereomeric palonosetron (VIII) or its hydrochloride (VIIIa) substantially free from unreduced intermediate (II) or (IIa) is crystallized from a suitable organic solvent to provide substantially pure palonosetron as its free base or hydrochloride (I).

The present invention further provides a process wherein the suitable organic solvent for the crystallisation of diastereomeric palonosetron (VIII) or its hydrochloride (VIIIa) substantially free from unreduced intermediate (II) or (IIa) respectively, is chosen from an alcoholic or a mixture of alcoholic solvents.

The alcoholic solvent may be chosen from a C-1 to C-8 linear or branched chain aliphatic alcohol, most preferably methanol and/or ethanol.

The present invention further provides a process wherein the crystallisation of diastereomeric palonosetron (VIII) or its hydrochloride (VIIIa) substantially free from unreduced intermediate (II) or (IIa) to the desired palonosetron hydrochloride (I), is optionally performed in the presence of the chosen halogenating agent.

The present invention further provides a process wherein the palonosetron hydrochloride (I) or its free base so obtained has NLT (not less than) 99.50% of the desired (3aS,S) isomer.

The present invention further provides a process wherein the palonosetron hydrochloride (I) or its free base so obtained has NMT (not more than) 0.40% of the undesired (3aR, S) isomer (Ia).

The present invention further provides a process wherein the palonosetron hydrochloride (I) or its free base so obtained is substantially free from the unreduced intermediate (IIa) and (II) respectively.

Thus the present invention provides an improved procedure for the preparation of substantially pure palonosetron and its acid addition salts which not only overcomes the problem of complete removal of unreduced intermediate (II) or its hydrochloride (IIa) present in varying amounts in the desired palonosetron and its hydrochloride (I) but also provides an improved procedure to produce palonosetron hydrochloride (I) in a reasonable yield and quality.

The following examples illustrate, but in no way limit the scopes of the novel process of this invention. Any deviation from this, apparent and obvious to a person skilled in the art of organic synthesis, forms part of this invention though not explicitly substantiated.

EXAMPLE 1

Preparation of Palonosetron Hydrochloride (I)

The diastereomeric palonosetron (VIII) (5.0 g) showing 54.06% of the desired (S, S) isomer, 42.13% of the undesired (3aR, S) isomer (Ia) and 1.04% of unreacted compound (IIa) was dissolved in 5% methanol in ethanol mixture (4.2 volumes). To it hydrochloric acid in ethanol was added and was heated to 70-75° C. Then neat liquid bromine (100 mg) was added at reflux. The solution was then cooled to 0 to 5° C. and 2.2 g of the precipitated crude palonosetron hydrochloride (I) was isolated by filtration. This obtained crude palonosetron hydrochloride (I) showing 96.41% of the desired (3aS, S) isomer, 3.59% of the undesired (3aR, S) isomer (Ia) and no unreacted compound (IIa) on HPLC, was then crystallized twice from ethanol-methanol mixture to give 1.5 g of the title product (I) which was found to contain 99.62% of the titled compound (I) and 0.38% (3aR, S) isomer (Ia) while no unreacted intermediate (IIa) could be detected by HPLC analysis.

EXAMPLE 2

(I) Preparation of Diastereomeric Palonosetrons (VIII)

(S)-2-(1-Azabicyclo[2.2.2]oct-3-yl)-2,4,5,6-tetrahydro-1H-benz[de]Isoquinoline-1-one hydrochloride (IIa) (20 g, 0.06 moles) was converted to its freebase (II) using 5.0% NaOH solution which was extracted by toluene. The toluene layer was concentrated under vacuum afforded 16.5 g of crude (II) which along with 20% Pd(OH)$_2$/C (16.5 g, 50.0% wet) in 23.0 volumes of ethyl acetate was stirred at 58.0° C. to 62° C. under a hydrogen atmosphere (30.0 atmospheres) for approximately 68.0 hours. The catalyst was then filtered and washed with ethyl acetate (20 ml) two times. The total ethyl acetate filtrate was then concentrated under vacuum to give 16.5 g of the title compound (VIII) which was found to contain 59.68% of the desired (3aS, S) isomer, 39.32% of undesired (3aR, S) isomer and 0.71% of unreacted intermediate (II) by HPLC analysis.

(II) Preparation of Palonosetron Hydrochloride (I)

The diastereomeric palonosetron (VIII) (16.5 g) obtained above was dissolved in 5% methanol in ethanol mixture (4.2 volumes). To it hydrochloric acid in ethanol was added and was heated to 70-75° C. Then N-bromosuccinimide (140 mg) was added at reflux. The solution was then cooled to 0 to 5° C. and 9.0 g of the precipitated crude palonosetron hydrochloride (I) were isolated by filtration. This obtained crude palonosetron hydrochloride (I) showing 95.90% of the desired (3aS,S) isomer, 3.10% of the undesired (3aR,S) isomer (Ia) and 0.04% of unreacted compound (IIa), when crystallized twice from ethanol-methanol mixture yielded 5.0 g of the title product (I) which was found to contain 99.66% of the titled compound (I), 0.29% of (3aR,S) isomer (Ia) and intermediate (IIa) below detection limit by HPLC analysis.
SOR: −94.0° (c=0.4 in water).
IR $v_{max}$ (KBr) cm$^{-1}$: 1645,1591.
$^1$H-NMR (500 MHz, CDCl3): δ 1.35-1.47 (m, 1H), 1.68-2.27 (m, 7H), 2.39-2.42 (m, 1H), 2.74-2.93 (m, 2H), 3.07-3.16 (m, 1H), 3.26-3.38 (m, 4H), 3.58-3.85 (m, 4H), 4.83-4.91 (m, 1H), 7.25-7.28 (m, 2H), 7.80-7.85 (m, 1H), 12.19 (S, 1H).

EXAMPLE 3

(I) Preparation of Diastereomeric Palonosetrons (VIII)

(S)-2-(1-Azabicyclo[2.2.2]oct-3-yl)-2,4,5,6-tetrahydro-1H-benz[de]Isoquinoline-1-one hydrochloride (IIa) (120 g, 0.36 moles) was converted to its freebase (II) using 5.0% NaOH solution and was extracted by toluene. The toluene layer was concentrated under vacuum afforded 99.0 g of crude (II) which along with 20% Pd(OH)$_2$/C (99.0 g, 50.0% wet) in 23.0 volumes of ethyl acetate was stirred at 58.0° C. to 62° C. under a hydrogen atmosphere (10.0 atmospheres) for approximately 25.0 hours. The catalyst was then filtered and washed with ethyl acetate (120 ml) two times. The total ethyl acetate filtrate was then concentrated under vacuum to give 96.0 g of the title compound (VIII) which was found to contain 56.36% of the desired (3aS, S) isomer, 42.14% of undesired (3aR, S) isomer and 0.51% of unreacted intermediate (II) by HPLC analysis.

(II) Preparation of Palonosetron Hydrochloride (I)

The diastereomeric palonosetron (VIII) (96.0 g) as obtained above was dissolved in 5% methanol in ethanol mixture (4.2 volumes). To it hydrochloric acid in ethanol was added and was heated to 70-75° C. Then N-bromosuccinimide (500 mg) was added at reflux. The solution was then cooled to 0 to 5° C. and 53.0 g of the precipitated crude palonosetron hydrochloride (I) were isolated by filtration. This obtained crude palonosetron hydrochloride (I) showing 93.74% of the desired (3aS,S) isomer, 6.19% of the undesired (3aR,S) isomer (Ia) and 0.2% of unreacted compound (IIa), when treated again with 200 mg of N-bromosuccinimide in ethanol-methanol mixture yielded 34.0 g of the title product (I) which was found to contain 99.63% of the titled compound (I), 0.32% of the undesired (3aR,S) isomer (Ia) and 0.05% of unreacted intermediate (IIa) by HPLC analysis.

EXAMPLE 4

(I) Preparation of Diastereomeric Palonosetrons (VIII)

(S)-2-(1-Azabicyclo[2.2.2]oct-3-yl)-2,4,5,6-tetrahydro-1H-benz[de]Isoquinoline-1-one hydrochloride (IIa) (11.0 g, 0.03 moles) was converted to its freebase (II) using 5.0% NaOH solution which was extracted by toluene. The toluene layer was concentrated under vacuum afforded 10.0 g of crude (II) which along with 20% Pd(OH)$_2$/C (10.0 g, 50.0% wet, first recovered catalyst) in 23.0 volumes of ethyl acetate was stirred at 58.0° C. to 62° C. under a hydrogen atmosphere (30.0 atmospheres) for approximately 94.0 hours. The catalyst was then filtered and washed with ethyl acetate (10 ml) two times. The total ethyl acetate filtrate was then concentrated under vacuum to give 10.0 g of the title compound (VIII) which was found to contain 59.60% of the desired (3aS,S) isomer, 36.15% of undesired (3aR,S) isomer and 2.74% of unreacted intermediate (II) by HPLC analysis.

(II) Preparation of Palonosetron Hydrochloride (I)

The diastereomeric palonosetron (VIII) (10.0 g) as obtained above was dissolved in 42.0 ml of 5% methanol in ethanol (4.2 volumes). To it hydrochloric acid in ethanol was added and was heated to 70-75° C. Then N-bromosuccinimide (200 mg) was added at reflux. The solution was then cooled to 0 to 5° C. and 5.5 g of the precipitated crude palonosetron hydrochloride (I) was isolated by filtration. This obtained crude palonosetron hydrochloride (I) showing 94.65% of the desired (3aS, S) isomer, 4.14% of the undesired (3aR, S) isomer (Ia) and 0.30% of unreacted compound (VI), when crystallized twice from ethanol-methanol mixture containing 20 mg of N-bromosuccinimide yielded 2.0 g of the title product (I) which was found to contain 99.60% of the titled compound (I), 0.40% (3aR, S) isomer (Ia) and intermediate (IIa) below detection limit by HPLC analysis.

We claim:

1. An improved and scalable process for the preparation of palonosetron and its acid addition salts, in particular hydrochloride (I) represented by the following structure with NMT (not more than) 0.40% of the undesired (3aR,S) isomer;

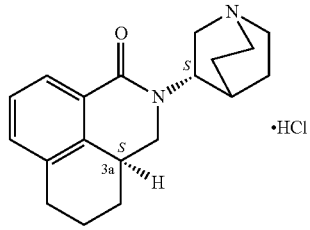

(I)

which comprises of, (a) converting intermediate (IIa) as such or as its freebase (II) to a crude mixture of diastereomeric palonosetrons (VIII) or (VIIIa) contaminated with varying amounts of unconverted intermediate (II) or (IIa) via hydrogenation under pressure with an appropriately chosen hydrogenation catalyst in an suitable organic solvent;

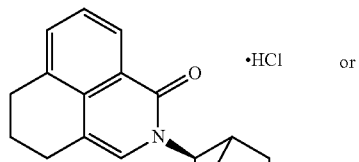

(II)

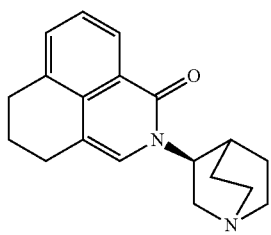

VIII

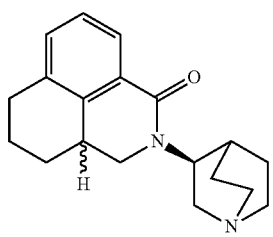

Diastereomers (R.S & S.S)

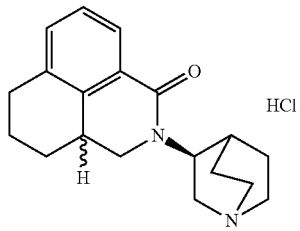

VIIIa

Diastereomers (R.S & S.S)

(b) treating the obtained crude diastereomeric palonosetrons (VIII) or hydrochloride (VIIIa) with a halogenating reagent chosen from bromine, chlorine, iodine, N-bromosuccinimide, N-chlorosuccinimide, N-iodosuccinimide, bromine-triphenylphosphine, chlorine-triphenylphosphine, N-bromophthalamide, N-chlorophthalimide in the presence or absence of free radical initiator to remove the unreduced intermediate II or IIa; and (c) finally, converting the resulting diastereomeric palonosetron (VIII) or its hydrochloride (VIIIa) to the desired palonosetron hydrochloride (I) via selective crystallization from a suitable single or mixture of organic solvents.

2. The process as claimed in claim 1, wherein the halogenating reagent is added neat or after dilution with the reaction solvent.

3. The process as claimed in claim 1, wherein the halogenating reagent is added at temperatures in the range of 25° C. to 75 ° C. of the reaction solvent.

4. The process as claimed in claim 1, wherein the organic solvent for performing the halogenation reaction is chosen from a $C_1$ to $C_8$ linear or branched aliphatic alcohol or a mixture of two or more $C_1$ to $C_8$ linear or branched aliphatic alcohol.

5. The process as claimed in claim 1, wherein the free radical initiator is benzyl peroxide or azobisisobutyronitrile.

6. The process as claimed in claim 1, wherein the halogenation reaction is carried out at ambient to reflux temperature of the chosen reaction medium.

7. The process as claimed in claim 1, wherein the halogenation reaction performed on the crude mixture of diastereomeric palonosetron (VIII) or its hydrochloride (VIIIa) contaminated with varying amounts of intermediate (II) or (IIa) to make it substantially free from unreacted intermediate (II) or (IIa) can be optionally performed more than once.

8. The process as claimed in claim 1, wherein the palonosetron or its hydrochloride (I) so obtained has NLT (not less than) 99.50% of the desired (3aS,S) isomer.

9. The process as claimed in claim 1, wherein the palonosetron or its hydrochloride (I) so obtained has NMT (not more than) 0.40% of the undesired (3aR,S) isomer (Ia).

* * * * *